(12) United States Patent
Ni et al.

(10) Patent No.: US 11,046,723 B2
(45) Date of Patent: Jun. 29, 2021

(54) PROCESS OF CONTROLLING THE IMPURITIES OF CLINDAMYCIN HYDROCHLORIDE

(71) Applicant: ZHAOKE (GUANGZHOU) Ophthalmic Drug Company Limited, Guangzhou (CN)

(72) Inventors: Dongsheng Ni, Guangzhou (CN); Jing Liu, Guangzhou (CN); Gang Li, Guangzhou (CN); Xiangrong Dai, Guangzhou (CN); Xiaoyi Li, Guangzhou (CN)

(73) Assignee: ZHAOKE (GUANGZHOU) Ophthalmic Drug Company Limited, Guangzhou (CN)

( * ) Notice: Subject to any disclaimer, the term of this patent is extended or adjusted under 35 U.S.C. 154(b) by 0 days.

(21) Appl. No.: 16/219,966

(22) Filed: Dec. 14, 2018

(65) Prior Publication Data

US 2019/0185505 A1    Jun. 20, 2019

(30) Foreign Application Priority Data

Dec. 14, 2017  (CN) .................. 201711336457.X

(51) Int. Cl.

| | | |
|---|---|---|
| *C07H 15/16* | (2006.01) | |
| *C07H 1/06* | (2006.01) | |
| *G01N 30/88* | (2006.01) | |
| *B01D 15/14* | (2006.01) | |
| *B01J 20/10* | (2006.01) | |
| *B01J 20/28* | (2006.01) | |
| *G01N 30/34* | (2006.01) | |
| *G01N 30/36* | (2006.01) | |
| *G01N 30/60* | (2006.01) | |

(52) U.S. Cl.
CPC ............ *C07H 15/16* (2013.01); *B01D 15/14* (2013.01); *B01J 20/103* (2013.01); *B01J 20/2803* (2013.01); *C07H 1/06* (2013.01); *G01N 30/88* (2013.01); *B01J 2220/54* (2013.01); *G01N 30/34* (2013.01); *G01N 30/36* (2013.01); *G01N 30/60* (2013.01); *G01N 2030/6013* (2013.01); *G01N 2030/8872* (2013.01)

(58) Field of Classification Search
CPC .................................. C07H 15/16; C07H 1/06
See application file for complete search history.

(56) References Cited

FOREIGN PATENT DOCUMENTS

CN          103487518 B          3/2015

OTHER PUBLICATIONS

Platzer et al., Journal of Pharmaceutical and Biomedical Analysis, 2006, 41, p. 84-88. (Year: 2006).*
Rao et al., Journal of Pharmaceutical and Biomedical Analysis, 2003, 33, p. 335-377. (Year: 2003).*

* cited by examiner

*Primary Examiner* — Jonathan S Lau

(57) ABSTRACT

The invention provides a process of controlling the impurities of clindamycin hydrochloride, comprising a step of purifying said clindamycin hydrochloride by two-phase high performance liquid chromatography, wherein the chromatographic conditions are as follows: the detection wavelength is 200-220 nm; the column temperature is 20-40° C.; the flow rate is 0.8-1 ml/min; Mobile phase A: 0.025 mol/L potassium dihydrogen phosphate solution; Mobile phase B: Acetonitrile; and gradient elution is performed. The method of controlling impurities of the invention can solve the problem of the interference by excipients and the problem of the separation of many impurities at the same time. It also provides an effective method for setting quality standard of impurities in such a formulation.

4 Claims, 2 Drawing Sheets
(2 of 2 Drawing Sheet(s) Filed in Color)

PROCESS OF CONTROLLING THE IMPURITIES OF CLINDAMYCIN HYDROCHLORIDE

CROSS-REFERENCE TO RELATED APPLICATIONS

The present application claims foreign priority of Chinese Patent Application No. 201711336457.X, filed on Dec. 14, 2017, the contents of which are hereby incorporated by reference.

BACKGROUND OF THE INVENTION

Clindamycin hydrochloride (Clindamycin hydrochloride) is a semi-synthetic derivative obtained by substituting a 7-position hydroxyl group of lincomycin hydrochloride with a chlorine atom. The antimicrobial spectrum is the same as that of lincomycin, and the antibacterial activity is 4-8 times higher than lincomycin. It is widely used in the treatment of infections caused by Gram-positive cocci such as *Staphyloccus aureus* and various anaerobic bacteria.

Clindamycin hydrochloride, its injection and compound gel showed more adverse reactions in clinical application. The adverse reactions of the drug in clinical use not only relate to the pharmacological activities of the drug itself, and are also associated with the presence of impurities in the drug. Any substance that affects the purity of a drug is called an impurity. In general, impurities refer to chemicals other than drug produced during production and storage. The impurities in the quality standard of medicines refer to impurities brought in by the production process and raw materials and excipents in accordance with the prescribed technology and the prescribed raw and excipents that have been examined and approved by the relevant drug supervisory and administrative authorities of the State according to law, or the degradation product produced in the storage process confirmed by the stability experiment.

Impurity detection is an important part in drug quality control, the content determination in the quality of the drugs refers to the determination of the contents of the main components in the raw materials and preparations, and related substances refer to organic impurities in the raw materials and preparations. Through the examination of related substances, we can find out the sources, properties, detection methods and their limits of the related substances, and it is possible to optimize such factors as the synthetic route, experimental conditions, and the like, thus avoiding the production or minimization of the related substance, to ensure and improve the quality of medicines in many ways, and to reduce adverse reactions of the drug.

The analysis method for determining the drug impurity should be sensitive and specific. The clindamycin hydrochloride as raw material has poor stability, therefore there are many impurities in clindamycin preparation that need to be monitored. Especially for clindamycin hydrochloride injection or gel preparation, since they comprises water and are unstable, a lot of degradation impurities need to be monitored during the effective period. If these impurities are not effectively controlled, the product will be at great risk. The Chinese Pharmacopoeia limits clindamycin only the total amount of impurities for clindamycin, the study on single impurity is not specific, while EU drug authorities and FDA both require the impurity which has an apparent content 0.1% or more in the clindamycin raw material medicine, to be identified on structure and verified on safety.

A single gel or a compound gel containing clindamycin, due to the complexity of the gel matrix and the strong UV peaks of the excipients, it is difficult to separate the excipient peaks from the impurity peaks, and the excipient interferes with the impurity, thus it presents a severe challenge to the method for impurity control content determination method for clindamycin hydrochloride for injection Chinese Patent No. CN201310392499.0 discloses a method of detecting impurities for Clindamycin hydrochloride for injection and determining the content thereof. The method can solve the problem of impurity separation, but it can not solve the problem of interference of excipient peak in gel preparation. Clindamycin hydrochloride in the national pharmacopoeia of various countries did not solve such a problem. In addition, for the analysis and detection methods published at domestic and abroad, less impurities are controlled, and even some impurities have not yet been identified.

The method of controlling Clindamycin impurities published by the raw material method of Clindamycin in Chinese pharmacopoeia can not control a plurality of known impurities in the gel at the same time, and there is a risk that the excipient peaks will interfere with the impurities. The analytical method is:

Chromatographic column: C18 chromatographic column (250×4.6 mm, 5 μm)
Phase A: 0.05M potassium dihydrogen phosphate (pH7.5)
Phase B: Acetonitrile
Column temperature: 30 degrees Celsius
Wavelength: 210 nm
Flow rate: 0.8 ml/min
Isocratic elution: 35 min (45% phase B)

The experimental diagram of adaptive resolution of impurity system is shown in FIG. 1. It can be seen from FIG. 1 that there are excipient peaks near the peak time of the impurities such as lincomycin and 7-epi-lincomycin in compound gel, when testing the excepients in the prescription at the same time. As the impurities are interfered by the excipients, it is impossible to judge whether or not other impurities are present therein. Therefore, it is desired to establish a new method for related substances, which can well seperate the excipient peaks from the impurity peaks.

SUMMARY OF THE INVENTION

An object of the invention is to provide a process of controlling the impurities of clindamycin hydrochloride comprising a step of purifying said clindamycin hydrochloride by two-phase high performance liquid chromatography, wherein the chromatographic conditions are as follows:

the detection wavelength is 200-220 nm;
the column temperature is 20-40° C.;
the flow rate is 0.8-1 ml/min;
Mobile phase A: 0.025 mol/L potassium dihydrogen phosphate solution;
Mobile phase B: Acetonitrile;
Gradient elution is performed based on the following gradient conditions: 0~35 min: 10%-25% phase B; 35~40 min: 10%-25%→30%-45% phase B; 40~78 min: 30%-45% phase B; 78~79 min: 30%-45%→10%-25% phase B; 79~90 min: 10%-25% phase B Preferably, the pH of mobile phase A is 7.5.
Preferably, the column temperature is 30° C.;
Preferably, the chromatographic column is filled with octadecylsilane-bonded silica gel (250 mm×4.6 mm, 5 μm). More preferably, the chromatographic column is a Waters chromatographic column, a Thermo chromatographic column, a Pheromone chromatographic column or a YMC chromatographic column.

Preferably, the detection wavelength is 210 nm.

More preferably, the gradient elution is performed based on the following gradient conditions: 0~35 min: 21% phase B; 35~40 min: 35% phase B; 40~78 min: 35% phase B; 78~79 min: 21% phase B; 79~90 min: 21% phase B.

The method of the invention can solve the problem of the interference by excipients and the problem of the separation of many impurities at the same time, and can provide a reasonable and scientific impurity limit according to the pharmacological toxicology and clinical experiment. It can provide a solution for the impurity control for clindamycin hydrochloride in the preparation, and it can also provide an effective method for setting quality standard of impurities in such a formulation.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

The invention discloses a process of controlling the impurities of clindamycin hydrochloride. Those skilled in the art can properly improve the process parameters in view of the contents herein. In particular, it is to be understood that all similar alternatives and modifications are obvious to those skilled in the art and are considered to be included in the present invention. The method of the invention has been described through a preferred embodiment. It is obvious for those skilled in the art that the method and application described herein may be modified or changed and combined to implement and apply the present invention without departing from the contents, spirit, and scope of the invention.

The invention is further described in combination with embodiments below:

EXAMPLE 1

Waters chromatographic column is filled with octadecyl-silane-bonded silica gel (250 mm×4.6 mm, 5 μm); the detection wavelength is 210 nm; the column temperature is 30° C.; the flow rate is 0.8 ml/min; Phase A, 0.025 mol/L potassium dihydrogen phosphate solution (adjusting pH to 7.5 with phosphoric acid), Phase B, Acetonitrile.

The flow rate is 1.0 ml/min, the wavelength is 210 nm. Phase A: 0.025 mol/L potassium dihydrogen phosphate solution (adjusting pH to 7.9)-Acetonitrile (78:28). Phase B: 0.025 mol/L potassium dihydrogen phosphate solution (adjusting pH to 2.5 with phosphoric acid)-methanol (19:81).

The gradient elution is as follows:

| Time (min) | A % | B % |
| --- | --- | --- |
| 0 | 100 | 0 |
| 12 | 100 | 0 |
| 14 | 0 | 100 |
| 28 | 0 | 100 |
| 31 | 100 | 0 |
| 40 | 100 | 0 |

Figure 1:
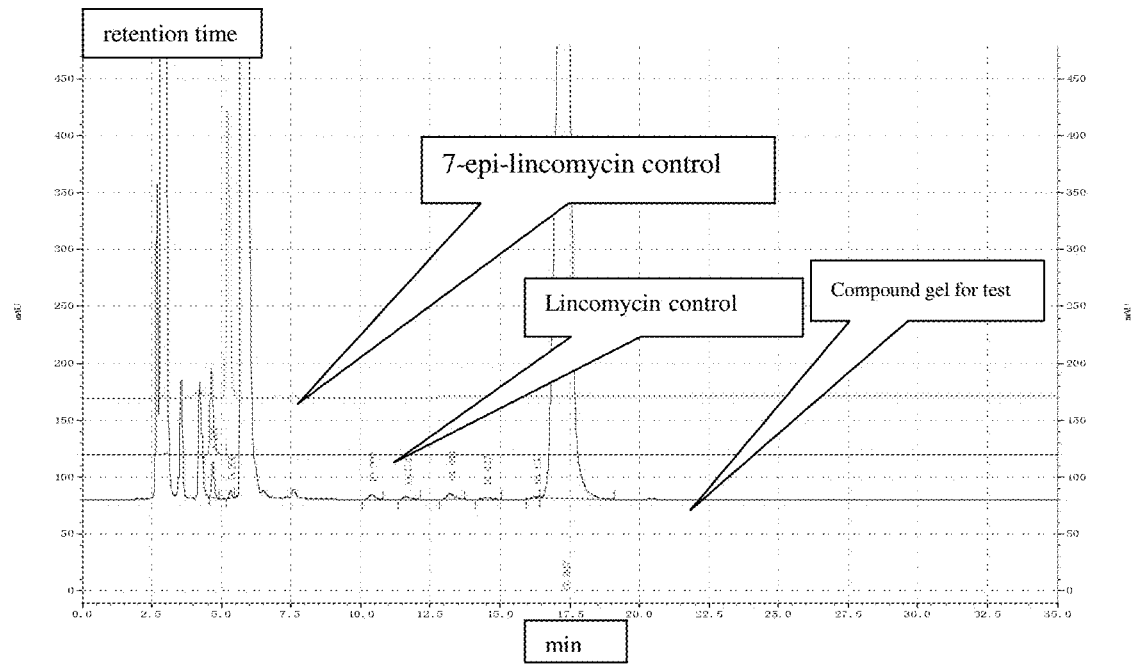
FIG. 1 is an experimental diagram of adaptive resolution of impurity system in Chinese Pharmacopoeia, wherein
Green: Lincomycin control solution;
Turquoise: 7-epi-lincomycin control solution;
Blue: Clindamycin compound gel sample for test.
Figure 2:
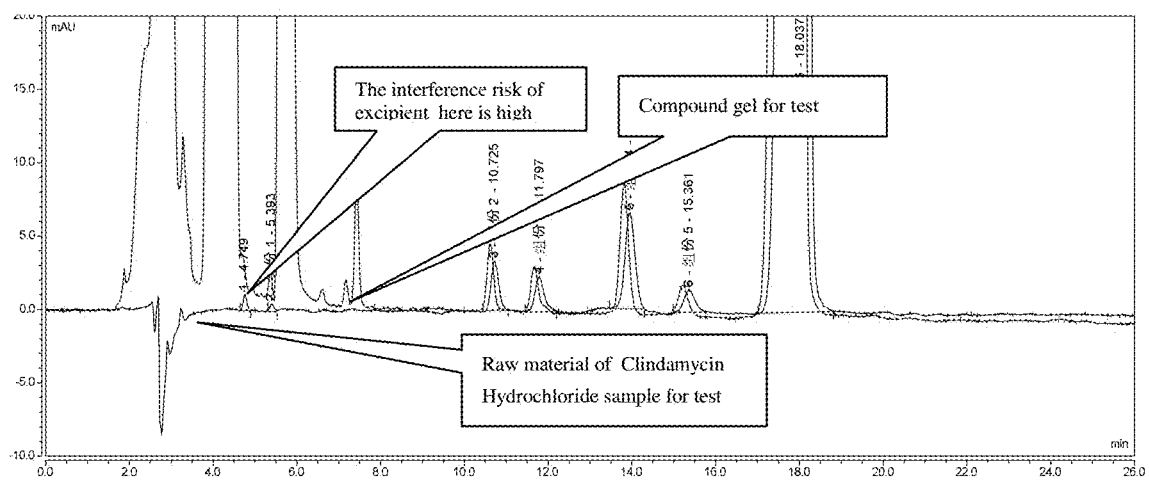
FIG. 2 is an experimental diagram of the adaptive resolution of the impurity System of Example 1, wherein
Black is the raw material of Clindamycin hydrochloride sample for test;
Blue is a compound gel sample for test.

As shown in FIG. 2, what is to be improved: excipient peaks at 4.7 min and 5.3 min interfere with the detection of impurities.

EXAMPLE 2

Chromatographic conditions:

Waters chromatographic column is filled with octadecyl-silane-bonded silica gel (250 mm×4.6 mm, 5 μm); the detection wavelength is 210 nm; the column temperature is 30° C.;

the flow rate is 0.8 ml/min; Phase A: 0.025 mol/L potassium dihydrogen phosphate solution (adjusting pH to 7.5 with phosphoric acid), Phase B, Acetonitrile.

The gradient elution is as follows:

| Time (min) | A % | B % |
| --- | --- | --- |
| 0 | 80 | 20 |
| 12 | 80 | 20 |
| 14 | 0 | 100 |
| 28 | 0 | 100 |
| 31 | 100 | 0 |
| 40 | 100 | 0 |

What is to be improved: Excipients, Lincomycin and 7-epi-lincomycin all have a peak, but the Lincomycin peak is positioned at the gradient peak, it's not at an appropriate position, the peak of excipient interfere with the detection of lincomycin and 7-epi-lincomycin.

EXAMPLE 3

Chromatographic conditions:

Waters chromatographic column is filled with octadecyl-silane-bonded silica gel (250 mm×4.6 mm, 5 μm); the detection wavelength is 210 nm; the column temperature is 30° C.; the flow rate is 0.8 ml/min; Phase A: 0.025 mol/L potassium dihydrogen phosphate solution (adjusting pH to 7.5 with phosphoric acid), Phase B, Acetonitrile.

The gradient elution is as follows:

| Time (min) | A % | B % |
| --- | --- | --- |
| 0 | 80 | 21 |
| 12 | 80 | 21 |
| 14 | 0 | 100 |
| 28 | 0 | 100 |

-continued

| Time (min) | A % | B % |
|---|---|---|
| 31 | 100 | 0 |
| 40 | 100 | 0 |

What is to be improved: Excipients, lincomycin and 7-epi-lincomycin all have a peak, the peak time is relatively appropriate, the excipient peak does not interfere with the detection of Lincomycin and 7-epi-lincomycin, the two impurities can also be effectively separated. However, the retention time for main peak is not appropriate, which needs to be readjusted.

EXAMPLE 4

Chromatographic conditions:

Waters chromatographic column is filled with octadecyl-silane-bonded silica gel (250 mm×4.6 mm, 5 μm); the detection wavelength is 210 nm; the column temperature is 30° C.; the flow rate is 0.8 ml/min; Phase A: 0.025 mol/L potassium dihydrogen phosphate solution (adjusting pH to 7.5 with phosphoric acid), Phase B, Acetonitrile.

The gradient elution is as follows:

| Time (min) | Phase A % | Phase B % |
|---|---|---|
| 0 | 75 | 25 |
| 35 | 75 | 25 |
| 37 | 65 | 30 |
| 75 | 65 | 30 |
| 76 | 75 | 25 |
| 86 | 75 | 25 |

What is to be improved: when B %=25% is used, the retention time for main peak of Clindamycin hydrochloride is more than 60 min, thus it shows that the proportion of organic phase was too small. Then the organic ratio is adjusted to B %=30%, however, clindamycin hydrochloride still have no peak within 52 min. Therefore, it is necessary to increase the proportion of organic phase.

EXAMPLE 5

Chromatographic conditions:

Waters chromatographic column is filled with octadecyl-silane-bonded silica gel (250 mm×4.6 mm, 5 μm); the detection wavelength is 210 nm; the column temperature is 30° C.; the flow rate is 0.8 ml/min; Phase A: 0.025 mol/L potassium dihydrogen phosphate solution (adjusting pH to 7.5 with phosphoric acid), Phase B, Acetonitrile.

The gradient elution is as follows:

| Time (min) | Phase A % | Phase B % |
|---|---|---|
| 0 | 79 | 21 |
| 35 | 79 | 21 |
| 37 | 65 | 35 |
| 75 | 65 | 35 |
| 76 | 79 | 21 |
| 86 | 79 | 21 |

Figure 3:
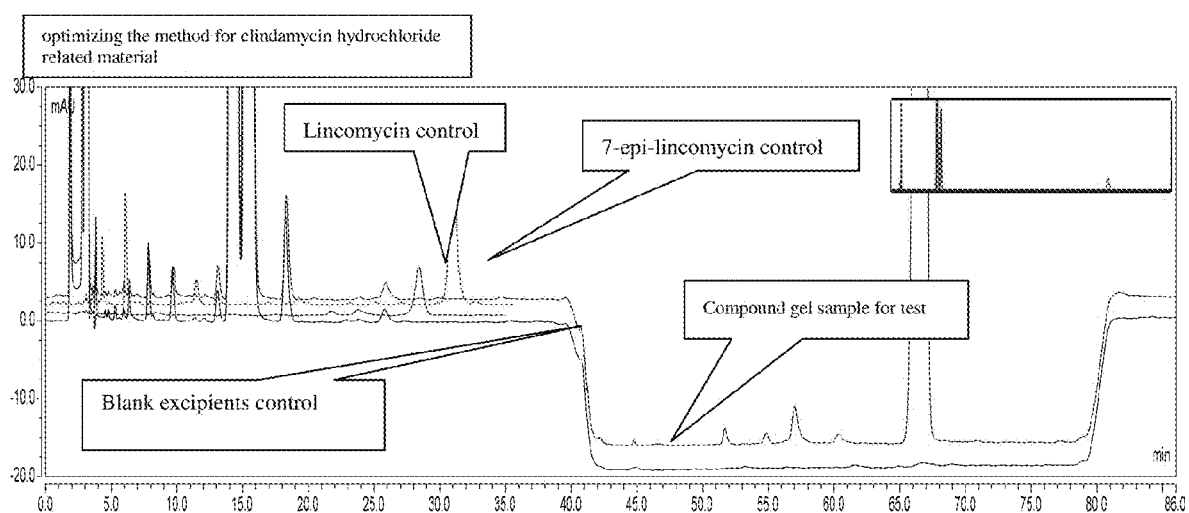
FIG. 3 shows the experimental diagram of adaptive resolution of impurity system in Example 5,
Black: blank excipents;
Blue: lincomycin control;
Red: 7-epi-lincomycin control;
Coffee color: Compound gel for test.

What is to be improved: it can be seen from FIG. 3 that the peak time of the impurity such as Lincomycin and 7-epi-lincomycin are appropriate, excipient peak does not interfere with impurity detection. From 35 minutes to 37 minutes the gradient rises too fast, and the gradient peak is too steep. Therefore, the time of gradient variation is prolonged, which makes the gradient change smoother. After adjusting the gradient change time to 5 minutes, it is the final gradient method.

The above is only preferable embodiments of the invention, it should be noted that a number of improvements and modifications may be made by those skilled in the art without departing from the principle of the invention, which should also be regarded as falling within the scope of protection of the present invention.

What is claimed is:

1. A process of controlling the impurities of clindamycin hydrochloride, comprising a step of purifying said clindamycin hydrochloride by two-phase high performance liquid chromatography, wherein the chromatographic conditions are as follows:
   the detection wavelength is 200-220 nm;
   the column temperature is 20-40° C., wherein the chromatographic column is filled with octadecylsilane-bonded silica gel (250 mm×4.6 mm, 5 μm);
   the flow rate is 0.8-1 ml/min;
   Mobile phase A: 0.025 mol/L potassium dihydrogen phosphate solution;
   the pH of Mobile phase A is 7.5;
   Mobile phase B: Acetonitrile;
   Gradient elution:
   Gradient elution is performed based on the following gradient conditions: 0-35 min: 10%-25% phase B; 35~40 min: 10%-25%→30%-45% phase B; 40~78 min: 30%-45% phase B; 78~79 min: 30%-45%→10%-25% phase B; 79~90 min: 10%-25% phase B.

2. The process of controlling the impurities according to claim 1, wherein the column temperature is 30° C.

3. The process of controlling the impurities according to claim 1, wherein the detection wavelength is 210 nm.

4. The process of controlling the impurities according to claim 1, wherein the gradient elution is performed based on the following gradient conditions: 0~35 min: 21% phase B; 35~40 min: 35% phase B; 40~78 min: 35% phase B; 78~79 min: 21% phase B; 79~90 min: 21% phase B.

* * * * *